(12) United States Patent
Oonuki et al.

(10) Patent No.: US 8,234,922 B2
(45) Date of Patent: Aug. 7, 2012

(54) ULTRASONIC DIAGNOSTIC EQUIPMENT

(75) Inventors: Yutaka Oonuki, Otawara (JP); Muneki Kataguchi, Nasushiobara (JP); Yasuhisa Makita, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 490 days.

(21) Appl. No.: 12/501,851

(22) Filed: Jul. 13, 2009

(65) Prior Publication Data

US 2010/0018314 A1    Jan. 28, 2010

(30) Foreign Application Priority Data

Jul. 22, 2008   (JP) ................ P2008-188926

(51) Int. Cl.
G01N 29/24 (2006.01)
A61B 8/14 (2006.01)
(52) U.S. Cl. ............ 73/602; 73/632; 600/443; 600/444; 600/447
(58) Field of Classification Search ............. 73/602, 73/632; 600/443–444, 447
See application file for complete search history.

(56) References Cited

FOREIGN PATENT DOCUMENTS

| JP | 4-8960 | | 1/1992 |
|---|---|---|---|
| JP | 5-188138 | | 7/1993 |
| JP | 05188138 A | * | 7/1993 |
| JP | 2006-26046 | | 2/2008 |

OTHER PUBLICATIONS

Office Action issued on Dec. 21, 2010 in the corresponding Chinese Patent Application No. 200910161605.8 (with Partial English Translation).

* cited by examiner

*Primary Examiner* — Peter MacChiarolo
*Assistant Examiner* — Rose M Miller
(74) *Attorney, Agent, or Firm* — Oblon, Spivak, McClelland, Maier & Neustadt, L.L.P.

(57) ABSTRACT

Provided is ultrasonic diagnostic equipment including: an equipment body; a display unit provided to the equipment body and configured to display an ultrasonic image; an equipment-side connector provided in the equipment body; and an ultrasonic probe having a probe-side connector to be connected to the equipment-side connector in a detachable manner. The ultrasonic probe is connected to the probe-side connector through a cable and configured to send and receive ultrasonic waves. The probe-side connector and the equipment-side connector are formed in structures capable of sending and receiving the ultrasonic waves even in the case of a 180-degree reverse connection of the probe-side connector to the equipment-side connector.

6 Claims, 4 Drawing Sheets

ULTRASONIC DIAGNOSTIC EQUIPMENT

CROSS REFERENCE OF THE RELATED APPLICATION

This application is based on and claims the benefit of priority from Japanese Patent Application No. 2008-188926, filed on Jul. 22, 2008; the entire contents of which are incorporated herein by reference.

BACKGROUND OF THE INVENTION

1. Field of the Invention

The present invention relates to ultrasonic diagnostic equipment.

2. Description of the Related Art

Ultrasonic diagnostic equipment is equipment which scans the inside of a subject using ultrasonic waves sent from an ultrasonic probe configured to send and receive ultrasonic waves, receives reflected waves (echo waves) from the inside of the subject, generates a reception signal by converting the intensity distribution of the reflected waves into brightness information, and forms an image indicating the internal state of the subject based on the generated reception signal (e.g., see JP-A No. 2006-26046(KOKAI)).

In general, the ultrasonic probe is detachably connected to the ultrasonic diagnostic equipment through a cable. The cable has a probe-side connector provided on one end thereof. The probe-side connector is for use in connection with the ultrasonic diagnostic equipment. This probe-side connector is inserted into an equipment-side connector of the ultrasonic diagnostic equipment, and thus the ultrasonic probe is electrically connected to the ultrasonic diagnostic equipment.

In general, however, the connection direction of the probe-side connector with respect to the equipment-side connector is fixed to one direction. That is, each of multiple pins of the equipment-side connector must be connected to a predetermined one of multiple pins of the probe-side connector.

For example, in portable compact ultrasonic diagnostic equipment, the connection direction of a probe-side connector is fixed to such a direction that a cable extending from the probe-side connector extends from the connecting portion toward a patient when the probe-side connector is in a connection completion state.

To an equipment body of such compact ultrasonic diagnostic equipment, a display unit (display) configured to display an ultrasonic image may be provided rotatably by using a two-axis hinge, or a display panel (display unit) may be provided in a slidable manner so as to cover an operation panel. Accordingly, in some cases, the ultrasonic diagnostic equipment is used in an upside down position. At the time of the use thereof in an upside down position, the ultrasonic diagnostic equipment is sometimes used at a position a certain distance above a floor by being hung on a wall or from a ceiling.

When the above-described compact ultrasonic diagnostic equipment is used in an upside down position, a cable extending from a probe-side connector first extends from the connecting portion in a direction (upward) opposite to that toward a patient and then extends toward the patient (downward). Since the cable first extends away from the patient, a cable length needed to perform smooth examination cannot be ensured. This results in poor operability. Further, in some cases, an operator forces the cable to move around and thus places a load on the cable.

SUMMARY OF THE INVENTION

An object of the present invention is to provide ultrasonic diagnostic equipment in which a reduction in operability can be prevented.

According to an aspect of the present invention, ultrasonic diagnostic equipment includes an equipment body, a display unit provided to the equipment body and configured to display an ultrasonic image, an equipment-side connector provided in the equipment body, and an ultrasonic probe having a probe-side connector to be connected to the equipment-side connector in a detachable manner. The ultrasonic probe is connected to the probe-side connector through a cable and configured to send and receive ultrasonic waves. The probe-side connector and the equipment-side connector are formed in structures capable of sending and receiving the ultrasonic waves even in the case of a 180-degree reverse connection of the probe-side connector to the equipment-side connector. The ultrasonic probe has a mechanism to indicate a 180-degree reverse connection of the probe-side connector to the equipment-side connector. The equipment body includes a unit configured to detect a 180-degree reverse connection of the probe-side connector to the equipment-side connector using the mechanism.

DESCRIPTION OF THE PREFERRED EMBODIMENTS

First Embodiment

A first embodiment of the present invention will be described with reference to FIGS. 1 to 3.

Figure 1:
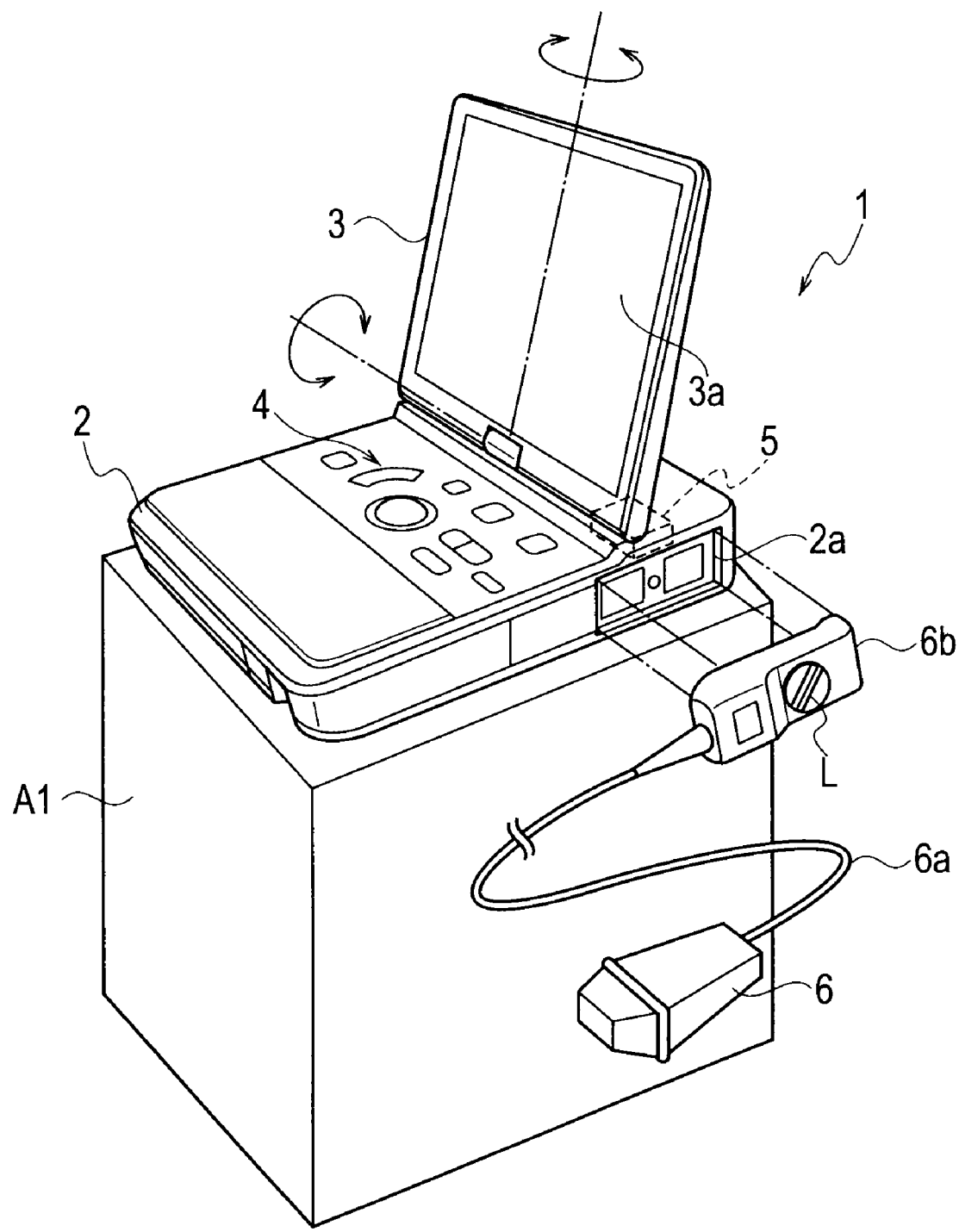
FIG. 1 is an external perspective view showing a schematic structure of ultrasonic diagnostic equipment according to a first embodiment of the present invention.
Figure 2:
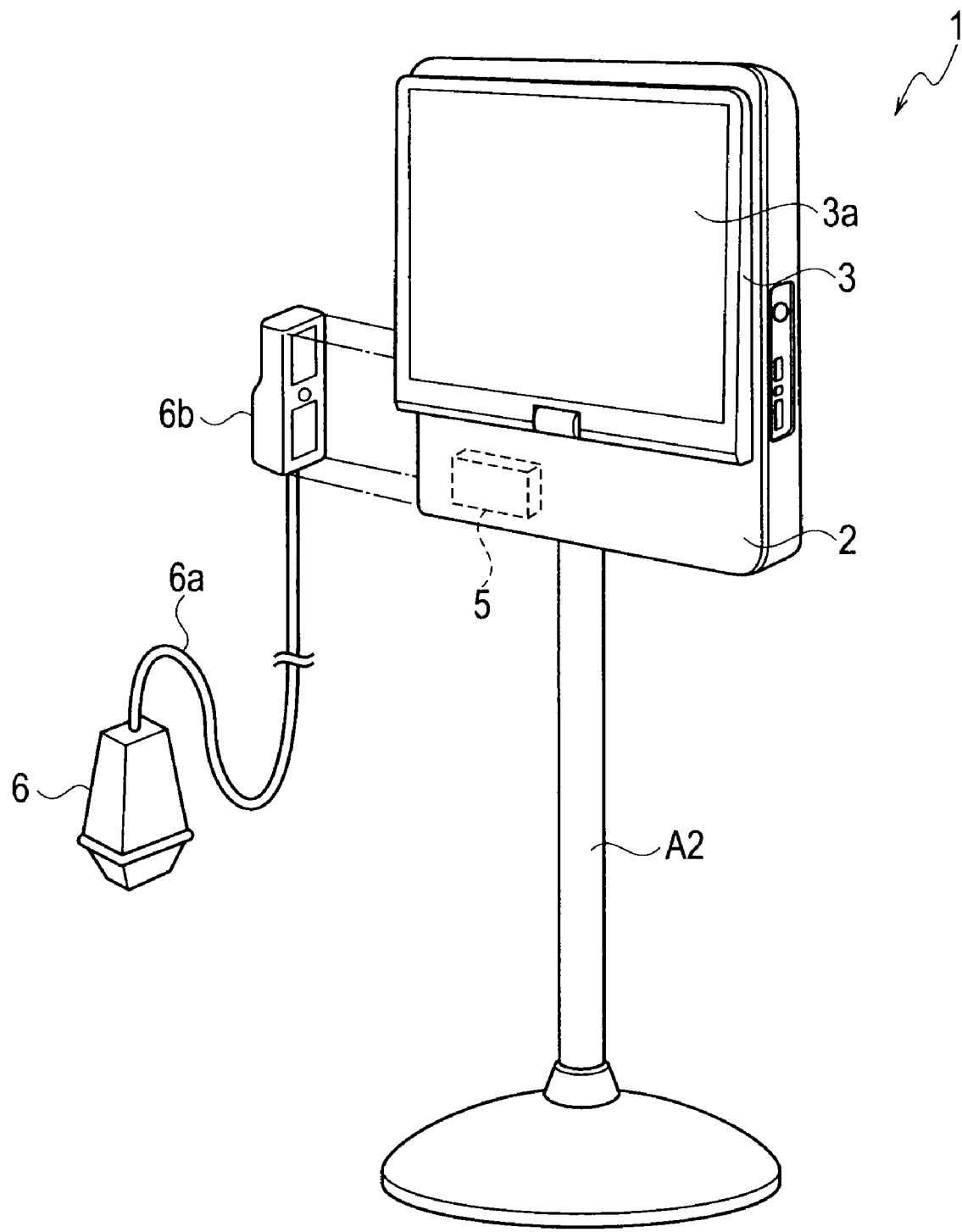
FIG. 2 is an external perspective view showing the ultrasonic diagnostic equipment shown in FIG. 1 which is in the state of being installed on a stand.

As shown in FIGS. 1 and 2, ultrasonic diagnostic equipment 1 according to the first embodiment of the present invention includes a portable compact equipment body 2, a display unit 3 rotatably provided to the equipment body 2 to display an image, an input unit 4 provided in the equipment body 2 to allow an operator such as a medical doctor to perform an input operation, and a controller 5 located within the equipment body 2 to control other units.

The equipment body 2 is an enclosure formed in a portable size. This equipment body 2 has an equipment-side connector 2a for connection in a side surface thereof. An ultrasonic probe 6 configured to send and receive ultrasonic waves is connected to this equipment-side connector 2a through a cable 6a and a probe-side connector 6b.

The ultrasonic probe 6 is connected through the cable 6a as a connecting cable to the probe-side connector 6b formed to be attachable and detachable to/from the equipment-side connector 2a of the equipment body 2. When the probe-side connector 6b is connected to the equipment-side connector 2a of the equipment body 2, the ultrasonic probe 6 is electrically connected to the ultrasonic diagnostic equipment 1 through the cable 6a and the probe-side connector 6b.

This ultrasonic probe 6 includes multiple ultrasonic transducers formed of material such as piezoelectric elements, and is a device configured to send ultrasonic waves to a subject with these ultrasonic transducers and to receive, as an echo signal, waves reflected from the subject. This ultrasonic probe 6 is applied to the surface of a subject such as a patient by an operator such as a medical doctor to send ultrasonic waves and receive reflected waves in this state.

The display unit 3 is a display device configured to display on a display screen 3a various images such as images (ultrasonic images) relating to a to-be-examined portion of the subject. This display unit 3 is provided to the equipment body 2 by using, for example, a two-axis hinge so as to be rotatable about two axes (see the directions indicated by arrows in FIG. 1). Thus, the facing direction of the display screen 3a can freely be changed. Further, the display unit 3 is disposed on the equipment body 2 in a way capable of covering the input unit 4 when being closed toward the equipment body 2. It should be noted that the display unit 3 may be, for example, a liquid crystal display or an organic electroluminescence (EL) display.

The ultrasonic diagnostic equipment 1 may, as shown in FIG. 1, be mounted on a supporting base A1 located beside a bed on which a subject such as a patient lies, or may, as shown in FIG. 2, be installed on a stand A2 serving as a supporting member, or may be installed at a predetermined height by being hung on a wall or from a ceiling. The equipment body 2 shown in FIG. 2 is in the state achieved by turning the equipment body 2 shown in FIG. 1 upside down. Specifically, the display unit 3 shown in FIG. 1 is turned by an operator so as to cover the input unit 4 with the display screen 3a facing outward, and is then closed toward the equipment body 2. Thereafter, the equipment body 2 is turned upside down, and then the ultrasonic diagnostic equipment 1 is installed on the stand A2 as shown in FIG. 2.

Referring back to FIG. 1, the input unit 4 is an operation unit configured to receive an input operation performed by an operator such as a medical doctor. This input unit 4 includes switches, buttons, a track ball, and the like. The operator performs an input operation with the input unit 4 in order to give various instructions to select an examination mode or a shooting mode, to start or stop shooting, and the like.

The controller 5 includes a central processing unit (CPU) configured to centrally control other units, a storage unit configured to store various programs and various kinds of information, and the like. This storage unit may be, for example, ROM (read-only memory), RAM (random access memory), flush memory, an HDD (hard disk drive), a recordable DVD (digital video disc or digital versatile disc) recorder, or the like.

This controller 5 generally reads and executes a boot program based on a BIOS to start an OS (operating system), which is basic software stored on the storage unit. Then, based on various programs and various kinds of data stored on the storage unit, the controller 5 executes a series of data processing steps for performing data calculation or manipulation or the like, an image displaying process for displaying an image, a shooting process for performing shooting, and the like.

In particular, the controller 5 sends a drive signal (electric pulse signal as an excitation signal) to the ultrasonic probe 6, receives a reflected signal (echo signal) from the ultrasonic probe 6, generates an image (image data such as B-mode image data or color Doppler image data) of a to-be-examined portion of a subject based on the received reflected signal, and displays the generated image on the display unit 3.

Next, the connection structure between the probe-side connector 6b of the ultrasonic probe 6 and the equipment-side connector 2a of the equipment body 2 will be described.

Figure 3:
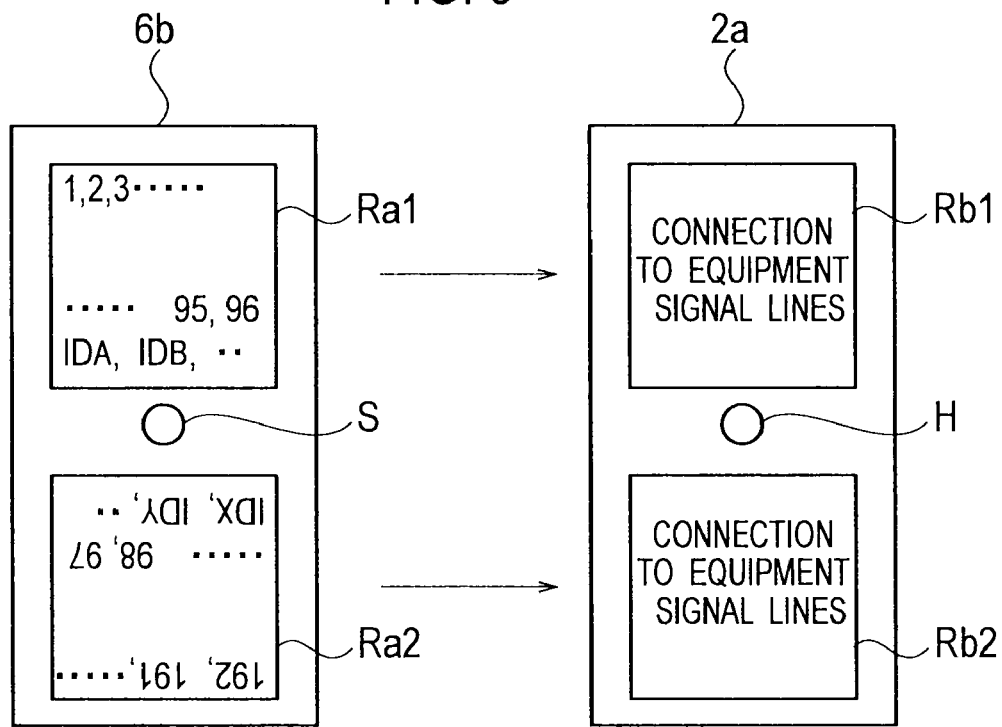
FIG. 3 is an explanatory diagram for explaining the connection structure between the ultrasonic diagnostic equipment shown in FIGS. 1 and 2 and an ultrasonic probe.

As shown in FIG. 3, the probe-side connector 6b and the equipment-side connector 2a are formed in structures capable of sending and receiving ultrasonic waves even in the case of a 180-degree reverse (rotation) connection of the probe-side connector 6b to the equipment-side connector 2a. At this time, the probe-side connector 6b is rotated 180 degrees in a plane orthogonal to the direction (insertion and removal direction) in which the probe-side connector 6b is attached or detached to/from the equipment-side connector 2a. That is, the connection direction of the probe-side connector 6b is reversed 180 degrees.

In the probe-side connector 6b, first and second signal blocks Ra1 and Ra2 are provided with a lock shaft S interposed therebetween. In these first and second signal blocks Ra1 and Ra2, multiple male pins (signal number: 1, 2, . . . , 191, 192, IDA, IDB, . . . , IDX, IDY, . . . ) are provided as contact terminals. These male pins are electrically connected to the ultrasonic probe 6 (respective ultrasonic transducers) through the cable 6a.

Also in the equipment-side connector 2a, first and second signal blocks Rb1 and Rb2 are provided with a lock hole H interposed therebetween. In these first and second signal blocks Rb1 and Rb2, multiple female pins are provided as contact terminals. These female pins are electrically connected to the controller 5 through equipment signal lines (not shown).

When the lock shaft S is turned in the state of being inserted in the lock hole H formed in the equipment-side connector 2a of the equipment body 2, a lock pin (not shown) provided on a tip-side portion of the lock shaft S in a protruding manner is caught in the lock hole H. This locks the probe-side connector 6b of the ultrasonic probe 6 into the equipment-side connector 2a. It should be noted that one end of the lock shaft S is fixed to a lever L (see FIG. 1) which can be turned by an operator. Accordingly, an operator turns the lever L to lock or unlock the probe-side connector 6b with respect to the equipment-side connector 2a.

The signal arrangement of the probe-side connector 6b is determined so that the arrangement of the terminals will be point symmetric about the rotation axis of the lock shaft S. Signals are arranged to be divided into two halves which are respectively on opposite sides with respect to the center of the symmetry. In the first signal block Ra1, which corresponds to one of the two halves, signal number sequentially increases, starting from the minimum of all the signal numbers, from the upper left toward the lower right in FIG. 3 in several rows, thus finally reaching the maximum of the smaller half (1 to 96) of all the signal numbers.

In the second signal block Ra2, which corresponds to the other of the two halves, signal number sequentially increases, starting from the minimum of the larger half of all the signal numbers, from the upper left toward the lower right in FIG. 3 in several rows, thus finally reaching the maximum of the larger half (97 to 192) of all the signal numbers. It should be noted that the signal corresponding to the maximum of all the signal numbers is arranged at a position symmetric to the signal corresponding to the minimum signal number.

To electrically identify a 180-degree reversal of the probe-side connector 6b, some of the terminals are given IDs (IDA, IDB, . . . , and IDX, IDY, . . . ), which are identification codes, thus enabling the detection of determination signals. This achieves a mechanism to indicate a 180-degree reverse connection of the probe-side connector 6b to the equipment-side connector 2a.

Using the determination signals corresponding to the above-described IDs, the controller 5 detects a 180-degree reverse connection of the probe-side connector 6b to the equipment-side connector 2a. If the controller 5 detects a 180-degree reverse connection of the probe-side connector 6b to the equipment-side connector 2a, the controller 5 performs changes relating to the display of an ultrasonic image to display the ultrasonic image in such a way that the ultrasonic image looks the same as that before a reversal of the probe-side connector 6b. For example, the controller 5 performs changes relating to the display of the ultrasonic image by reversing data when sending data to a display system or writing data to memory where the data is to be stored.

Alternatively, if the controller 5 detects a 180-degree reverse connection of the probe-side connector 6b to the equipment-side connector 2a, the controller 5 performs changes (e.g., reverses sending and receiving) relating to the sending and receiving of ultrasonic waves to display the ultrasonic image in such a way that the ultrasonic image looks the same as that before a reversal of the probe-side connector 6b.

Next, the attachment of the ultrasonic probe 6 to the aforementioned ultrasonic diagnostic equipment 1 will be described.

As shown in FIG. 1, when the ultrasonic diagnostic equipment 1 is mounted on the supporting base A1, the probe-side connector 6b is connected to the equipment-side connector 2a in such a way that the cable 6a extending from the probe-side connector 6b extends from the connecting portion toward a patient (toward the front of the equipment). This ensures a cable length needed to perform smooth examination, and thus allows an operator such as a medical doctor to comfortably perform examination using the ultrasonic probe 6.

As shown in FIG. 2, also when the ultrasonic diagnostic equipment 1 is installed on the stand A2 (the equipment body 2 shown in FIG. 2 is in the state achieved by turning the equipment body 2 shown in FIG. 1 upside down), the probe-side connector 6b is connected to the equipment-side connector 2a in such a way that the cable 6a extending from the probe-side connector 6b extends from the connecting portion toward a patient (downward). This ensures a cable length needed to perform smooth examination even in the state in which the equipment body 2 is turned upside down, and thus allows an operator such as a medical doctor to comfortably perform examination using the ultrasonic probe 6.

In conventional connection, the equipment body 2 used in an upside down position has poor operability because the cable 6a extends away from a patient. In contrast, the equipment body 2 employing the above-described connection structure has operability similar to that before the equipment body 2 is turned upside down because the cable 6a extends toward a patient even in the case of the upside down position. Further, the extension of the cable 6a toward a patient prevents an operator from forcing the cable 6a to move around and thus placing a load on the cable 6a.

Moreover, even when the equipment body 2 is used in an upside down position, a reversal of the probe-side connector 6b is detected, and an ultrasonic image is displayed in such a way that the ultrasonic image looks the same as that before a reversal of the probe-side connector 6b. This prevents a mirror reversal of an ultrasonic image that would occur in the case of a 180-degree reverse connection of the probe-side connector 6b to the equipment-side connector 2a.

As described above, according to the first embodiment of the present invention, the probe-side connector 6b of the ultrasonic probe 6 and the equipment-side connector 2a of the equipment body 2 are formed in structures capable of sending and receiving ultrasonic waves even in the case of a 180-degree reverse connection of the probe-side connector 6b to the equipment-side connector 2a. Accordingly, even when, for example, the equipment body 2 is used in an upside down position, the probe-side connector 6b can be connected to the equipment-side connector 2a in such a way that the cable 6a extending from the probe-side connector 6b extends from the connecting portion toward a patient (downward). This causes the cable 6a to extend toward a patient, and provides operability similar to that before the equipment body 2 is turned upside down. Thus, a reduction in operability can be prevented.

Further, a unit configured to detect a 180-degree reverse connection of the probe-side connector 6b to the equipment-side connector 2a is provided. When the unit detects such connection, changes relating to the display of an ultrasonic image or changes relating to the sending and receiving of ultrasonic waves are performed to display the ultrasonic image in such a way that the ultrasonic image looks the same as that before a reversal of the probe-side connector 6b. Accordingly, even when the equipment body 2 is used in an upside down position, a reversal of the probe-side connector 6b is detected, and an ultrasonic image is displayed in such a way that the ultrasonic image looks the same as that before a reversal of the probe-side connector 6b. This prevents a mirror reversal of an ultrasonic image that would occur due to a reverse connection of the probe-side connector 6b.

Second Embodiment

A second embodiment of the present invention will be described with reference to FIG. 4.

The second embodiment of the present invention is basically the same as the first embodiment. Accordingly, in the second embodiment, portions different from those of the first embodiment will be described. It should be noted that in the second embodiment, the same portions as those of the first embodiment will not be described.

Figure 4:
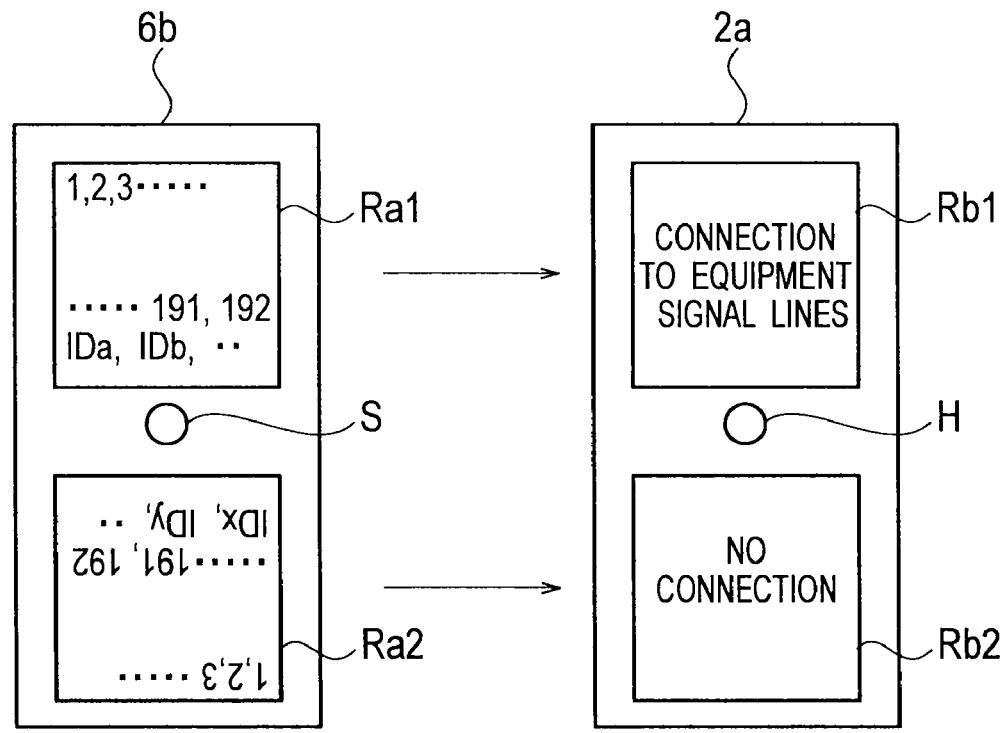
FIG. 4 is an explanatory diagram for explaining the connection structure between the ultrasonic diagnostic equipment according to a second embodiment of the present invention and an ultrasonic probe.

As shown in FIG. 4, in the second embodiment of the present invention, the probe-side connector 6b and the equipment-side connector 2a are formed in structures capable of sending and receiving ultrasonic waves and also displaying an ultrasonic image in such a way that the ultrasonic image looks the same as that before a reversal of the probe-side connector 6b even in the case of a 180-degree reverse connection of the probe-side connector 6b to the equipment-side connector 2a. At this time, the probe-side connector 6b is reversed 180 degrees in a plane orthogonal to the direction (insertion and removal direction) in which the probe-side connector 6b is attached or detached to/from the equipment-side connector 2a. In other words, the connection direction of the probe-side connector 6b is reversed 180 degrees.

In the first signal block Ra1, multiple male pins (signal number: 1, 2, . . . , 191, 192, IDa, IDb, . . . ) are provided as contact terminals, whereas, in the second signal block Ra2, multiple male pins (signal number: 1, 2, . . . , 191, 192, IDx, IDy, . . . ) are provided as contact terminals. These male pins are electrically connected to the ultrasonic probe 6 (respective ultrasonic transducers) through the cable 6a.

In the first and second signal blocks Rb1 and Rb2, multiple female pins are provided as contact terminals. The female pins of the first signal block Rb1 are electrically connected to the controller 5 through equipment signal lines (not shown), but the female pins of the second signal block Rb2 are not electrically connected to the controller 5.

The signal arrangement of the probe-side connector 6b is determined so that the arrangement of the terminals will be point symmetric about the rotation axis of the lock shaft S. Signals are arranged in the same manner in each of two blocks Ra1 and Ra2 which are respectively on opposite sides with respect to the center of the symmetry. In the first signal block Ra1, signal number sequentially increases, starting from the minimum of all the signal numbers, from the upper left toward the lower right in FIG. 4 in several rows, thus finally reaching the maximum (1 to 192) of all the signal numbers.

Also in the second signal block Ra2, signal number sequentially increases, starting from the minimum signal number, from the upper left toward the lower right in FIG. 4 in several rows, thus finally reaching the maximum signal number (1 to 192).

To electrically identify a 180-degree reversal of the probe-side connector 6b, some of the terminals are given IDs (IDa, IDb, . . . , and IDx, IDy, . . . ), which are identification codes, thus enabling the detection of determination signals. This achieves a mechanism to indicate a 180-degree reverse connection of the probe-side connector 6b to the equipment-side connector 2a.

In conventional connection, the equipment body 2 used in an upside down position has poor operability because the cable 6a extends away from a patient. In contrast, the equipment body 2 employing the above-described connection structure has operability similar to that before the equipment body 2 is turned upside down because the cable 6a extends toward a patient even in the case of the upside down position.

Moreover, even when the equipment body 2 is used in the upside down position, the same connection as that before the equipment body 2 is turned upside down can be obtained. This prevents a mirror reversal of an ultrasonic image that would occur in the case of a 180-degree reverse connection of the probe-side connector 6b to the equipment-side connector 2a.

As described above, according to the second embodiment of the present invention, effects similar to those of the first embodiment can be obtained. Further, even when the equipment body 2 is used in an upside down position, the same connection as that before the equipment body 2 is turned upside down can be obtained. This prevents a mirror reversal of an ultrasonic image that would occur due to a reverse connection of the probe-side connector 6b.

Third Embodiment

A third embodiment of the present invention will be described with reference to FIG. 5.

The third embodiment of the present invention is basically the same as the first embodiment. Accordingly, in the third embodiment, portions different from those of the first embodiment will be described. It should be noted that in the third embodiment, the same portions as those of the first embodiment will not be described.

Figure 5:
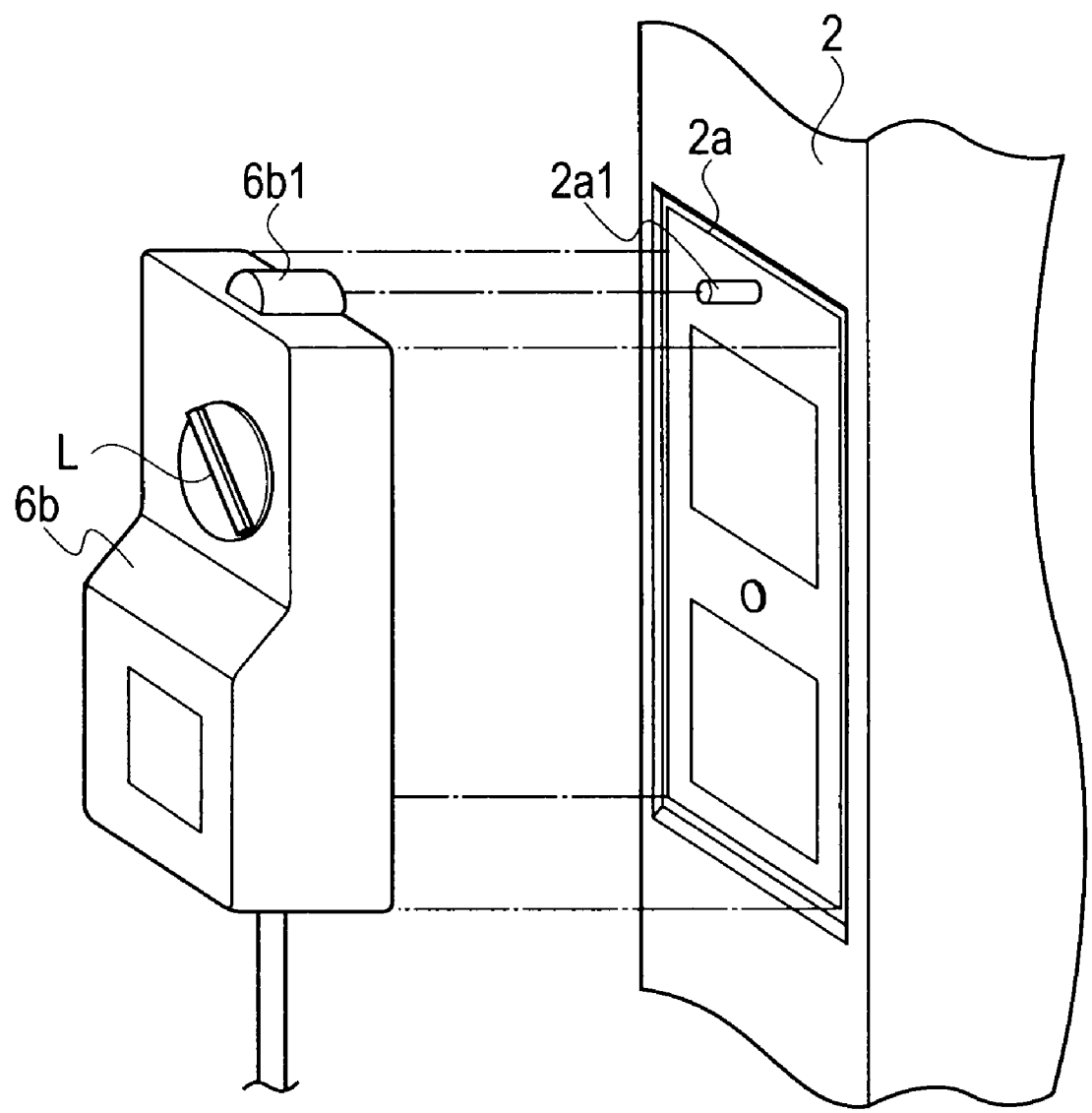
FIG. 5 is an explanatory diagram for explaining the connection structure between the ultrasonic diagnostic equipment according to a third embodiment of the present invention and an ultrasonic probe.

As shown in FIG. 5, in the third embodiment of the present invention, a protruding portion 6b1 is provided on a side surface of the probe-side connector 6b, and a retractable pin 2a1 is provided in the equipment-side connector 2a. This pin 2a1 is pushed in by the protruding portion 6b1 in the state in which the probe-side connector 6b is connected to the equipment-side connector 2a. The pin 2a1 functions as a switch for detecting a reversal of the probe-side connector 6b. When the pin 2a1 is pushed in, the controller 5 determines that the probe-side connector 6b is connected to the equipment-side connector in the state of being reversed 180 degrees, and displays an ultrasonic image in such a way that the ultrasonic image looks the same as that before a reversal of the probe-side connector 6b, as in the first embodiment. In this case, with the protruding portion 6b1, a mechanism to indicate a 180-degree reverse connection of the probe-side connector 6b to the equipment-side connector 2a can be achieved.

It should be noted that though the reversal detection is performed with the protruding portion 6b1 and the pin 2a1 in this embodiment, the present invention is not limited to this. For example, the detection may be performed optically or magnetically. Further, though the reversal detection is performed on the ultrasonic diagnostic equipment 1 side, the present invention is not limited to this. The reversal detection may be performed on the ultrasonic probe 6 side.

As described above, according to the third embodiment of the present invention, effects similar to those of the first embodiment can be obtained. In addition, in comparison with the first embodiment, a reversal of the probe-side connector 6b can be detected with a simple structure without providing the ID terminals.

Other Embodiments

It should be noted that the present invention is not limited to the above-described embodiments, and various changes can be made thereto without departing from the spirit thereof. For example, some of the components described in the above-described embodiments may be omitted. Further, components described in different embodiments may appropriately be used in combination.

What is claimed is:

1. An ultrasonic diagnostic equipment comprising:
an equipment body;
a display unit provided to the equipment body and configured to display an ultrasonic image;
an equipment-side connector provided in the equipment body; and
an ultrasonic probe including a probe-side connector to be connected to the equipment-side connector in detachable manner, the ultrasonic probe being connected to the probe-side connector through a cable and configured to send and receive ultrasonic waves, wherein
the probe-side connector and the equipment-side connector are formed in structures capable of sending and receiving the ultrasonic waves even in the case of a 180-degree reverse connection of the probe-side connector to the equipment-side connector,
the ultrasonic probe includes a detection mechanism to detect electrical signals indicating a 180-degree reverse connection of the probe-side connector to the equipment-side connector,
the equipment body includes a detection unit configured to detect the 180-degree reverse connection of the probe-side connector to the equipment-side connector based on the electrical signals detected by the detection mechanism, and
the equipment body includes a display changing unit configured to perform, if the 180-degree reverse connection of the probe-side connector to the equipment-side connector is detected by the detection unit, changes relating to display of the ultrasonic image, and to display the ultrasonic image such that the ultrasonic image looks the same as that before a reversal of the probe-side connector.

2. The ultrasonic diagnostic equipment according to claim 1, wherein
the detection mechanism includes a protruding portion provided on the probe-side connector, and
the detection unit includes a switch provided in the equipment-side connector and configured to be pushed in by the protruding portion in a state in which the probe-side connector is connected to the equipment-side connector.

3. The ultrasonic diagnostic equipment according to claim 1, wherein the detection unit includes an optical or magnetic switch provided in the equipment-side connector and configured to be turned on in a state in which the probe-side connector is connected to the equipment-side connector.

4. An ultrasonic diagnostic equipment comprising:
an equipment body;
a display unit provided to the equipment body and configured to display an ultrasonic image;
an equipment-side connector provided in the equipment body; and
an ultrasonic probe including a probe-side connector to be connected to the equipment-side connector in detachable manner, the ultrasonic probe being connected to the probe-side connector through a cable and configured to send and receive ultrasonic waves, wherein
the probe-side connector and the equipment-side connector are formed in structures capable of sending and receiving the ultrasonic waves even in the case of a 180-degree reverse connection of the probe-side connector to the equipment-side connector,
the ultrasonic probe includes a detection mechanism for detecting electrical signals indicating a 180-degree reverse connection of the probe-side connector to the equipment-side connector,
the equipment body includes a detection unit configured to detect the 180-degree reverse connection of the probe-side connector to the equipment-side connector based on the electrical signals detected by the detection mechanism, and
the equipment body includes a transmission changing unit configured to perform, if the 180-degree reverse connection of the probe-side connector to the equipment-side connector is detected by the detection unit, changes relating to sending and receiving of the ultrasonic waves, and to display the ultrasonic image such that the ultrasonic image looks the same as that before a reversal of the probe-side connector.

5. The ultrasonic diagnostic equipment according to claim 4, wherein
the detection mechanism includes a protruding portion provided on the probe-side connector, and
the detection unit includes a switch provided in the equipment-side connector and configured to be pushed in by the protruding portion in a state in which the probe-side connector is connected to the equipment-side connector.

6. The ultrasonic diagnostic equipment according to claim 4, wherein the detection unit includes an optical or magnetic switch provided in the equipment-side connector and configured to be turned on in a state in which the probe-side connector is connected to the equipment-side connector.

\* \* \* \* \*